(12) United States Patent
Flanagan et al.

(10) Patent No.: US 10,709,433 B2
(45) Date of Patent: Jul. 14, 2020

(54) LARGE BORE VASCULAR CLOSURE SYSTEM

(71) Applicant: BOSTON SCIENTIFIC SCIMED, INC., Maple Grove, MN (US)

(72) Inventors: Aiden Flanagan, County Galway (IE); Niamh Hynes, Galway (IE); Tim O'Connor, Galway (IE); Fergal Horgan, County Mayo (IE); Michael G. Hayes, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 232 days.

(21) Appl. No.: 15/712,769

(22) Filed: Sep. 22, 2017

(65) Prior Publication Data
US 2018/0085101 A1 Mar. 29, 2018

Related U.S. Application Data

(60) Provisional application No. 62/398,858, filed on Sep. 23, 2016.

(51) Int. Cl.
*A61B 17/00* (2006.01)
*A61B 17/30* (2006.01)
(Continued)

(52) U.S. Cl.
CPC ...... *A61B 17/0057* (2013.01); *A61B 17/0218* (2013.01); *A61B 17/0401* (2013.01); *A61B 17/0469* (2013.01); *A61B 17/0682* (2013.01); *A61B 17/072* (2013.01); *A61B 17/30* (2013.01); *A61B 17/1152* (2013.01); *A61B 2017/0065* (2013.01); *A61B 2017/00349* (2013.01);
(Continued)

(58) Field of Classification Search
CPC ...... A61B 17/0057; A61B 2017/00668; A61B 17/0644; A61B 2017/00637; A61B 17/064; A61B 17/068; A61B 17/10; A61B 17/0218; A61B 17/072; A61B 17/1152; A61B 2017/308
See application file for complete search history.

(56) References Cited

U.S. PATENT DOCUMENTS

| 6,524,326 B1 | 2/2003 | Zhu et al. |
| 6,964,675 B2 | 11/2005 | Zhu et al. |

(Continued)

FOREIGN PATENT DOCUMENTS

| EP | 1667748 B1 | 5/2011 |
| WO | 2008031102 A1 | 3/2008 |

OTHER PUBLICATIONS

International Search Report and Written Opinion dated Nov. 30, 2017 for International Application No. PCT/US2017/052936.

*Primary Examiner* — Katherine M Shi
(74) *Attorney, Agent, or Firm* — Seager, Tufte & Wickhem LLP

(57) ABSTRACT

A vascular closure system for sealing an opening in a blood vessel may include an introducer sheath extending through the opening, the introducer sheath having a lumen extending through the introducer sheath, wherein partial withdrawal of the introducer sheath from the opening everts tissue of the blood vessel at the opening, and a shaping sheath slidably disposed over the introducer sheath, the shaping sheath having a split distal portion configured to engage the everted tissue.

11 Claims, 20 Drawing Sheets

(51) Int. Cl.
*A61B 17/04* (2006.01)
*A61B 17/02* (2006.01)
*A61B 17/068* (2006.01)
*A61B 17/072* (2006.01)
*A61B 17/11* (2006.01)
*A61B 17/115* (2006.01)

(52) U.S. Cl.
CPC ............... *A61B 2017/00557* (2013.01); *A61B 2017/00659* (2013.01); *A61B 2017/00663* (2013.01); *A61B 2017/00668* (2013.01); *A61B 2017/00876* (2013.01); *A61B 2017/00884* (2013.01); *A61B 2017/0409* (2013.01); *A61B 2017/0464* (2013.01); *A61B 2017/07214* (2013.01); *A61B 2017/07228* (2013.01); *A61B 2017/1142* (2013.01); *A61B 2017/306* (2013.01); *A61B 2017/308* (2013.01)

(56) References Cited

U.S. PATENT DOCUMENTS

| | | | |
|---|---|---|---|
| 7,060,084 B1 | 6/2006 | Loshakove et al. | |
| 7,670,348 B2 | 3/2010 | Hausen et al. | |
| 7,727,245 B2 | 6/2010 | Bender et al. | |
| 7,753,250 B2 | 7/2010 | Clauson et al. | |
| 7,766,208 B2 | 8/2010 | Epperly et al. | |
| 8,048,108 B2 | 11/2011 | Sibbitt, Jr. et al. | |
| 8,066,720 B2 | 11/2011 | Knodel et al. | |
| 8,192,459 B2 | 6/2012 | Cummins et al. | |
| 8,469,995 B2 | 6/2013 | Cummins et al. | |
| 8,486,092 B2 | 7/2013 | Carley et al. | |
| 8,486,108 B2 | 7/2013 | Carley et al. | |
| 8,585,836 B2 | 9/2013 | Carley et al. | |
| 8,590,760 B2 | 11/2013 | Cummins et al. | |
| 8,690,910 B2 | 4/2014 | Carley et al. | |
| 8,702,730 B2 | 4/2014 | Shriver | |
| 8,728,119 B2 | 5/2014 | Cummins | |
| 8,758,397 B2 | 6/2014 | Sibbitt, Jr. et al. | |
| 8,821,534 B2 | 9/2014 | Voss | |
| 8,920,442 B2 | 12/2014 | Sibbitt, Jr. et al. | |
| 8,956,388 B2 | 2/2015 | Ginn et al. | |
| 9,149,276 B2 | 10/2015 | Voss | |
| 9,172,644 B2 | 10/2015 | Meloche | |
| 9,271,707 B2 | 3/2016 | Palermo et al. | |
| 9,364,209 B2 | 6/2016 | Voss | |
| 2004/0153122 A1 | 8/2004 | Palermo | |
| 2006/0106405 A1* | 5/2006 | Fann | A61B 17/11 606/142 |
| 2007/0049968 A1 | 3/2007 | Sibbitt, Jr. et al. | |
| 2008/0065152 A1* | 3/2008 | Carley | A61B 17/0644 606/215 |
| 2008/0147112 A1* | 6/2008 | Sheets | A61B 17/00491 606/205 |
| 2011/0230897 A1 | 9/2011 | Palermo et al. | |
| 2012/0296374 A1 | 11/2012 | Ziobro et al. | |
| 2014/0172013 A1 | 6/2014 | Burbank et al. | |
| 2015/0142049 A1 | 5/2015 | Delgado et al. | |
| 2016/0157841 A1 | 6/2016 | Coleman et al. | |
| 2016/0158044 A1 | 6/2016 | Chou et al. | |

* cited by examiner

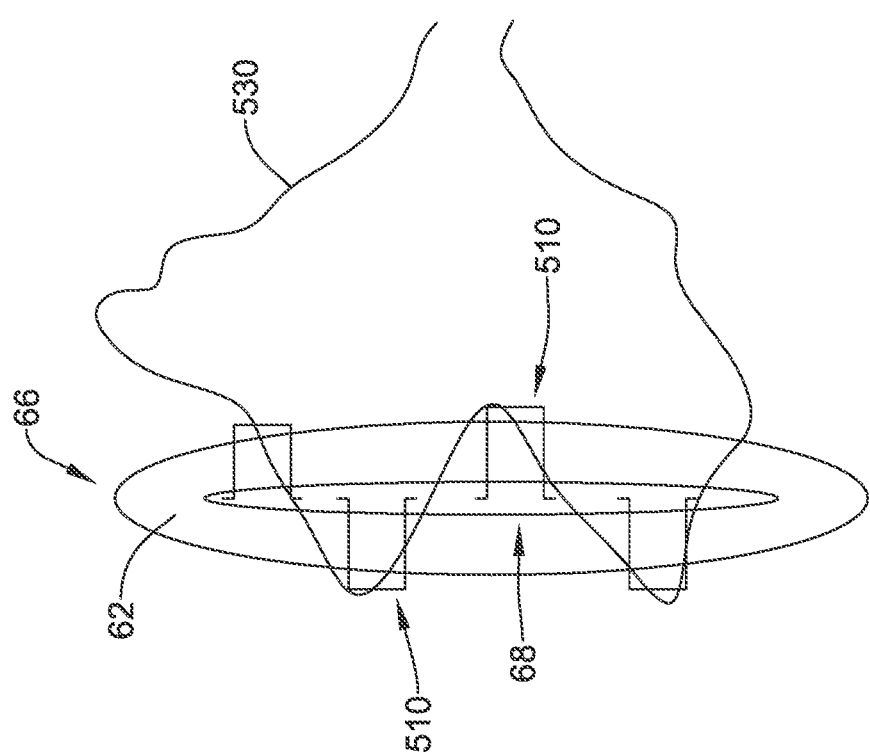

LARGE BORE VASCULAR CLOSURE SYSTEM

CROSS REFERENCE TO RELATED APPLICATIONS

This application claims benefit of the provisional U.S. Patent Application No. 62/398,858, filed Sep. 23, 2016, which is hereby incorporated by reference in its entirety.

TECHNICAL FIELD

The present disclosure pertains to medical devices, and methods for manufacturing and/or using medical devices. More particularly, the present disclosure pertains to methods and devices for closing and/or sealing punctures in tissue.

BACKGROUND

In percutaneous medical procedures, an opening may be created in a wall of a blood vessel to allow for the insertion of various medical devices which can be navigated through the blood vessel to a site to be treated. For example, after initial access into the blood vessel is obtained, a medical device may be inserted through the tissue tract created between the skin, or epidermis, of the patient down through the subcutaneous tissue and into the opening formed in the blood vessel. The medical device may then be navigated through the blood vessel to the treatment site.

Once the procedure is completed, the medical device(s) or other equipment introduced into the blood vessel may be retracted from the body through the blood vessel, out the opening in the wall of the blood vessel, and out through the tissue tract. The physician or other medical technician is presented with the challenge of trying to close the opening in the blood vessel and/or the tissue tract formed in the epidermis and subcutaneous tissue. A number of different device structures, assemblies, and methods are known for closing the opening in the blood vessel and/or tissue tract, each having certain advantages and disadvantages. There is an ongoing need to provide alternative medical devices as well as alternative methods for manufacturing and/or using medical devices.

SUMMARY

In a first aspect, a vascular closure system for sealing an opening in a blood vessel may comprise an introducer sheath extending through the opening, the introducer sheath having a lumen extending through the introducer sheath, wherein partial withdrawal of the introducer sheath from the opening everts tissue of the blood vessel at the opening, and a shaping sheath slidably disposed over the introducer sheath, the shaping sheath having a split distal portion configured to engage the everted tissue.

In addition or alternatively, and in a second aspect, the shaping sheath includes a concave distal end configured to engage an outer surface of the blood vessel.

In addition or alternatively, and in a third aspect, each side of the split distal portion of the shaping sheath is biased radially inward.

In addition or alternatively, and in a fourth aspect, the split distal portion engages the everted tissue to form a seam oriented transverse to a longitudinal axis of the blood vessel.

In addition or alternatively, and in a fifth aspect, the shaping sheath includes a suction rim at a distal end of the shaping sheath configured to secure the split distal portion to the everted tissue.

In addition or alternatively, and in a sixth aspect, the vascular closure system may further comprise a stapler configured to be slidably disposed within the shaping sheath for fastening the everted tissue.

In addition or alternatively, and in a seventh aspect, the stapler comprises multiple parallel staplers each configured to deploy one or more staples into the everted tissue.

In addition or alternatively, and in an eighth aspect, the stapler is configured to deploy multiple staples in series into the everted tissue.

In addition or alternatively, and in a ninth aspect, withdrawal of the introducer sheath and the percutaneous medical device from within the shaping sheath permits the split distal portion to translate the everted tissue to bring an inner surface of the blood vessel into contact with itself.

In addition or alternatively, and in a tenth aspect, the vascular closure system may further comprise a percutaneous medical device configured to be slidably disposed within the lumen to perform an intravascular procedure, the introducer sheath includes an enlargeable portion proximate a distal end of the introducer sheath.

In addition or alternatively, and in an eleventh aspect, the enlargeable portion of the introducer sheath extends radially outward from the introducer sheath at a maximum outer extent of the enlargeable portion.

In addition or alternatively, and in a twelfth aspect, the vascular closure system may further comprise a dilator configured to be slidably received within the lumen of the introducer sheath, wherein the dilator includes an enlargeable portion proximate a tapered distal end of the dilator.

In addition or alternatively, and in a thirteenth aspect, the enlargeable portion of the dilator is configured to extend radially outward from the introducer sheath after the enlargeable portion of the dilator has been passed through the introducer sheath.

In addition or alternatively, and in a fourteenth aspect, withdrawal of the dilator from within the shaping sheath permits the split distal portion to translate the everted tissue to bring an inner surface of the blood vessel into contact with itself.

In addition or alternatively, and in a fifteenth aspect, a method of closing an opening in a blood vessel may comprise inserting an introducer sheath into a lumen of the blood vessel through the opening, wherein the introducer sheath includes a lumen configured to accept a percutaneous medical device for insertion into the lumen of the blood vessel for performing an intravascular procedure; partially withdrawing the introducer sheath from the lumen of the blood vessel, thereby everting tissue of the blood vessel at the opening; advancing a shaping sheath over the introducer sheath to the opening, the shaping sheath having a split distal portion that engages the everted tissue; withdrawing the introducer sheath from within the shaping sheath; advancing a stapler within the shaping sheath to the everted tissue; and deploying multiple staples into the everted tissue while the everted tissue is being engaged by the shaping sheath.

In addition or alternatively, and in a sixteenth aspect, the deployed staples are oriented with a body of the staples parallel to a longitudinal axis of the lumen of the blood vessel.

In addition or alternatively, and in a seventeenth aspect, the introducer sheath includes an enlargeable portion proximate a distal end of the introducer sheath, wherein the enlargeable portion of the introducer sheath extends radially outward from the introducer sheath at the enlargeable portion's maximum extent.

In addition or alternatively, and in an eighteenth aspect, each side of the split distal portion of the shaping sheath is self-biased radially inwardly.

In addition or alternatively, and in a nineteenth aspect, a method of closing an opening in a blood vessel may comprise inserting an introducer sheath into a lumen of the blood vessel through the opening, wherein the introducer sheath includes a lumen configured to accept a percutaneous medical device for insertion into the lumen of the blood vessel for performing an intravascular procedure; advancing a dilator into the lumen of the blood vessel through the introducer sheath until an enlargeable portion proximate a tapered distal end of the dilator is disposed distal of the introducer sheath; partially withdrawing the dilator from the lumen of the blood vessel, wherein the enlargeable portion extends radially outward of the introducer sheath thereby everting tissue of the blood vessel at the opening; advancing a shaping sheath over the introducer sheath to the opening, the shaping sheath having a split distal portion that engages the everted tissue; withdrawing the dilator and the introducer sheath through the shaping sheath; advancing a stapler within the shaping sheath to the everted tissue; and deploying multiple staples into the everted tissue while the everted tissue is being engaged by the shaping sheath.

In addition or alternatively, and in a twentieth aspect, withdrawal of the dilator through the shaping sheath permits the split distal portion to translate the everted tissue to bring an inner surface of the blood vessel into contact with itself.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which:

FIGS. 18-20 illustrate an example configuration for closing an opening in a blood vessel.

Figure 1:
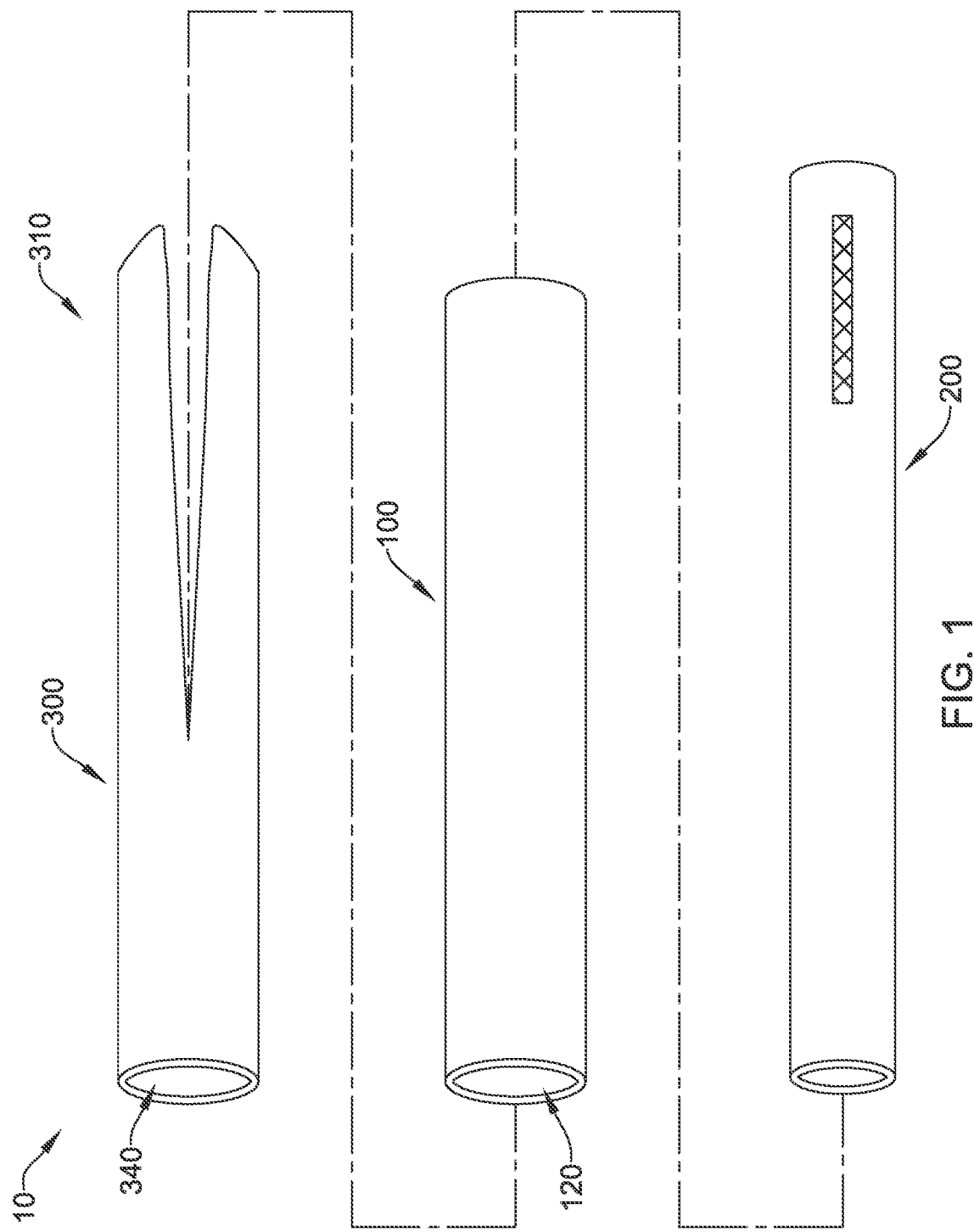
FIG. 1 is a schematic view of an example vascular closure system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Disclosed herein are apparatus, medical devices, and/or methods that may be used to diagnose, treat, and/or repair a portion of the cardiovascular system. At least some of the apparatus, medical devices, and/or methods disclosed herein may include and/or be used to close and/or seal an opening or puncture in a blood vessel. While discussed below in the context of a blood vessel, the apparatus, medical devices, and/or methods may be applied and/or used with other tubular structures, vessels, organs, etc. The devices and methods disclosed herein may also provide a number of additional desirable features and/or benefits as described in more detail below.

FIG. 1 illustrates an example vascular closure system 10 that may be used for sealing an opening in a wall of a blood vessel or other tubular structure. In some embodiments, a vascular closure system 10 may include an introducer sheath 100 having a lumen 120 extending therethrough, a percutaneous medical device 200, and/or a shaping sheath 300. The introducer sheath 100 may be configured to extend through the opening in the wall of the blood vessel or other tubular structure. In at least some embodiments, the percutaneous medical device 200 (e.g., a catheter, trocar, dilator, endoscope, delivery device, a catheter assembly including an implant, etc.) may be configured to be slidably disposed within the lumen 120 of the introducer sheath 100 to perform an intravascular procedure at a target site within a blood vessel or other tubular structure. For example, in some embodiments, the percutaneous medical device 200 may be an assembly comprising a delivery catheter having a medical implant (e.g., a stent, a filter device, a replacement heart valve, etc.) disposed within the delivery catheter. In some embodiments, the percutaneous medical device 200 may be removed from the introducer sheath 100 prior to closure of the opening in the wall of the blood vessel or other tubular structure. In some embodiments, partial withdrawal of the introducer sheath 100 from the opening in the wall of the blood vessel may evert tissue of the blood vessel or other tubular structure at the opening, as discussed below. The shaping sheath 300 may include a lumen 340 extending therethrough. The shaping sheath 300 may be configured to be slidably disposed over and/or around the introducer sheath 100. The shaping sheath 300 may have a split distal portion 310 configured to engage and/or grip the everted tissue of the blood vessel or other tubular structure at the opening, as discussed below.

Figure 2:
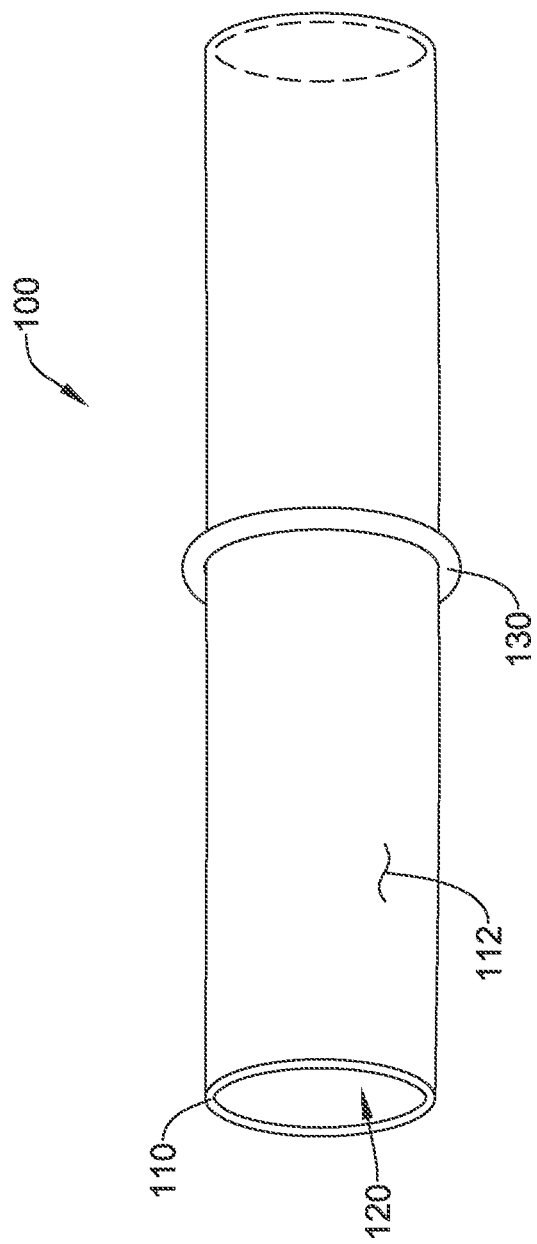
FIG. 2 illustrates an example introducer sheath.

In some embodiments, the introducer sheath 100 may have an outer wall 110 defining a lumen 120 extending through the introducer sheath 100 from a proximal end to a distal end, as seen in FIG. 2 for example. In some embodiments, an introducer sheath 100 may include an opening or side passageway extending through the outer wall 110 of the introducer sheath 100 and in fluid communication with the lumen 120. In some embodiments, the introducer sheath 100 may include an enlargeable portion 130 proximate the distal end of the introducer sheath 100. In some embodiments, the enlargeable portion 130 may be integrally formed with the introducer sheath 100. In some embodiments, the enlargeable portion 130 may be added, attached, and or secured to an outer surface 112 of the outer wall 110 of the introducer sheath 100. In some embodiments, the enlargeable portion 130 may comprise an o-ring, an inflatable annular balloon, an expandable flange, or other expandable structure disposed on and/or about the outer wall 110 of the introducer sheath 100. In some embodiments, the inflatable annular balloon may integrated into and/or integrally formed with an outer layer of the introducer sheath 100.

In some embodiments, the enlargeable portion 130 may have and/or assume an everting configuration wherein the enlargeable portion 130 of the introducer sheath 100 extends radially outward from the introducer sheath 100 at a maximum outer extent of the enlargeable portion 130. In other words, the enlargeable portion 130 may have a maximum outer extent greater than and/or larger than an outer extent of the introducer sheath 100 at a position along the outer wall 110 of the introducer sheath 100 where the enlargeable portion 130 is located. In some embodiments, the maximum outer extent of the enlargeable portion 130 may be greater than and/or larger than a maximum outer extent of the introducer sheath 100.

Figure 3:
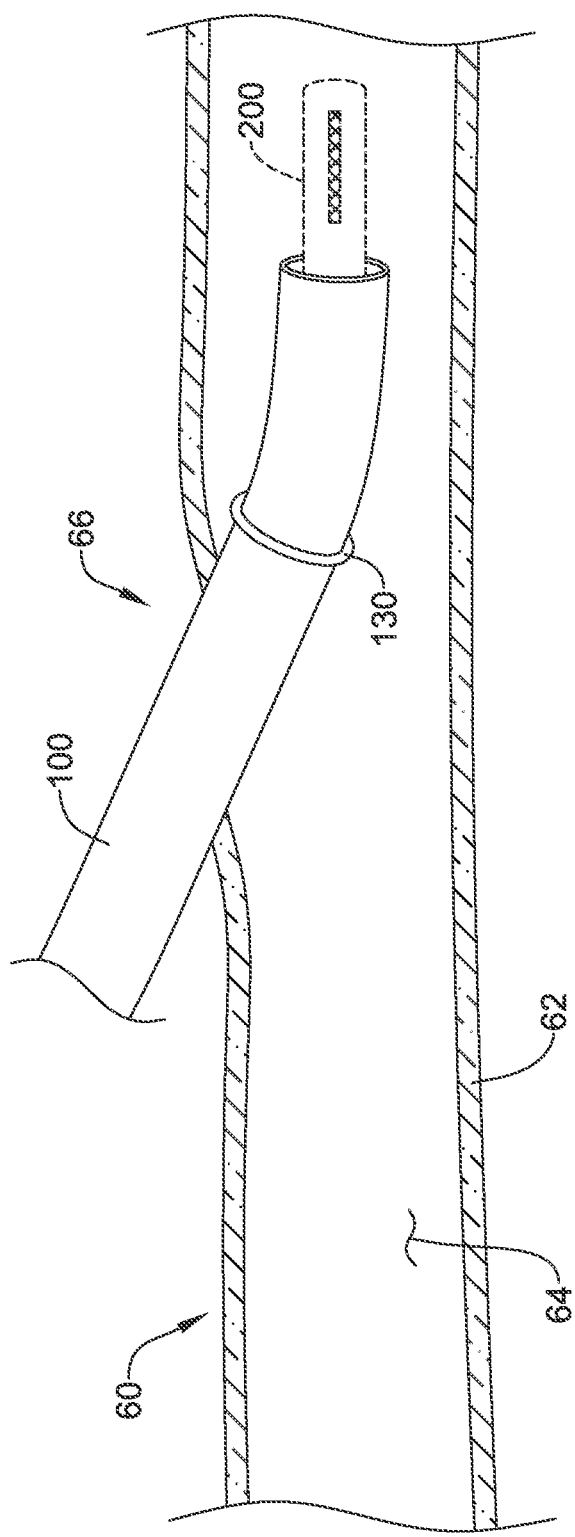
FIG. 3 illustrates the example introducer sheath of FIG. 2 extending through an opening in a blood vessel wall.

As may be seen in FIG. 3 for example, the introducer sheath 100 may extend through an opening 66 in a wall 62 of a blood vessel 60 or other tubular structure. The introducer sheath 100 may be used as a conduit to access a lumen 64 of the blood vessel 60 or other tubular structure with a percutaneous medical device 200 (shown in phantom) to perform an intravascular procedure at a target site. Upon completion of the procedure, the percutaneous medical device 200 may be removed and closure of the opening 66 in the wall 62 of the blood vessel 60 or other tubular structure may be effected. In some embodiments, closure of the opening 66 in the wall 62 of the blood vessel 60 may be preceded by placing the enlargeable portion 130 of the introducer sheath 100 into the everting configuration, as seen in FIG. 3 for example. In some embodiments, placing the enlargeable portion 130 of the introducer sheath 100 into the everting configuration may include expanding and/or inflating the enlargeable portion 130 (if capable thereof) such that the enlargeable portion 130 extends radially outward from the outer wall 110 of the introducer sheath 100. In the everting configuration, the enlargeable portion 130 may contact, engage, and/or otherwise pull tissue of the blood vessel 60 or other tubular structure outward (e.g., evert) at the opening 66 in the wall 62 of the blood vessel 60 or other tubular structure as the introducer sheath 100 is withdrawn from the lumen 64 of the blood vessel 60 or other tubular structure through the opening 66 in the wall 62 of the blood vessel 60 or other tubular structure.

Figure 4:
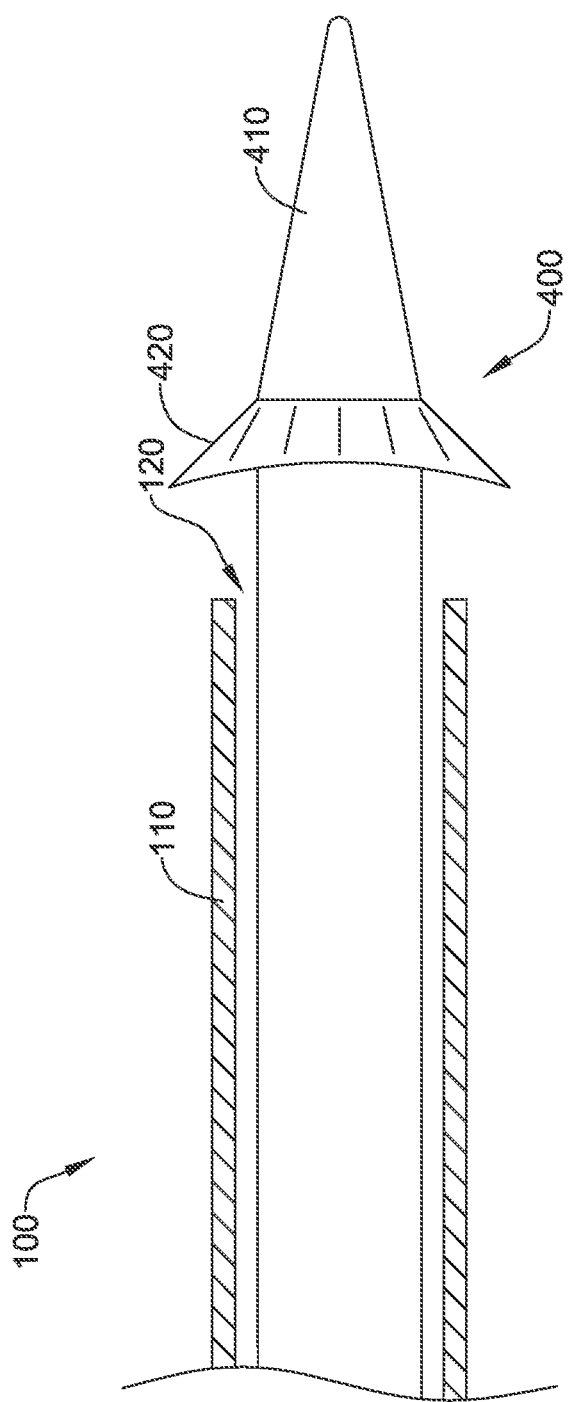
FIG. 4 illustrates an example introducer sheath.

FIG. 4 illustrates an example introducer sheath 100 including a dilator 400 configured to be slidably disposed within the lumen 120 of the introducer sheath 100. In some embodiments, the dilator 400 may comprise a solid shaft, a tubular member having a lumen therethrough, and/or combinations thereof. In some embodiments, the dilator 400 may include a tapered distal end 410, wherein an outer diameter of the dilator 400 may decrease in a distal direction toward the distal end 410. In some embodiments, the dilator 400 may include an enlargeable portion 420 proximate the tapered distal end 410 of the dilator 400. In general, the enlargeable portion 420 may be disposed proximal of the tapered distal end 410 of the dilator 400. In some embodiments, the enlargeable portion 420 may comprise an inflatable annular balloon, an expandable flange, or other actuatable and/or expandable structure disposed on and/or about an outer surface of the dilator 400. In use, the dilator 400 may be slidingly extended through the lumen 120 of the introducer sheath 100, after a percutaneous medical device 200 has been removed therefrom, until the enlargeable portion 420 is disposed distal of the introducer sheath 100. In some embodiments, the enlargeable portion 420 of the dilator 400 may be configured to extend radially outward from the introducer sheath 100 in an everting configuration after the enlargeable portion 420 of the dilator 400 has been passed through the introducer sheath 100. In some embodiments, the enlargeable portion 420 may have a maximum outer extent greater than and/or larger than an outer extent of the introducer sheath 100 at the distal end of the introducer sheath 100 (e.g., where the enlargeable portion 420 is located). In some embodiments, the maximum outer extent of the enlargeable portion 420 may be greater than and/or larger than a maximum outer extent of the introducer sheath 100.

Figure 5:
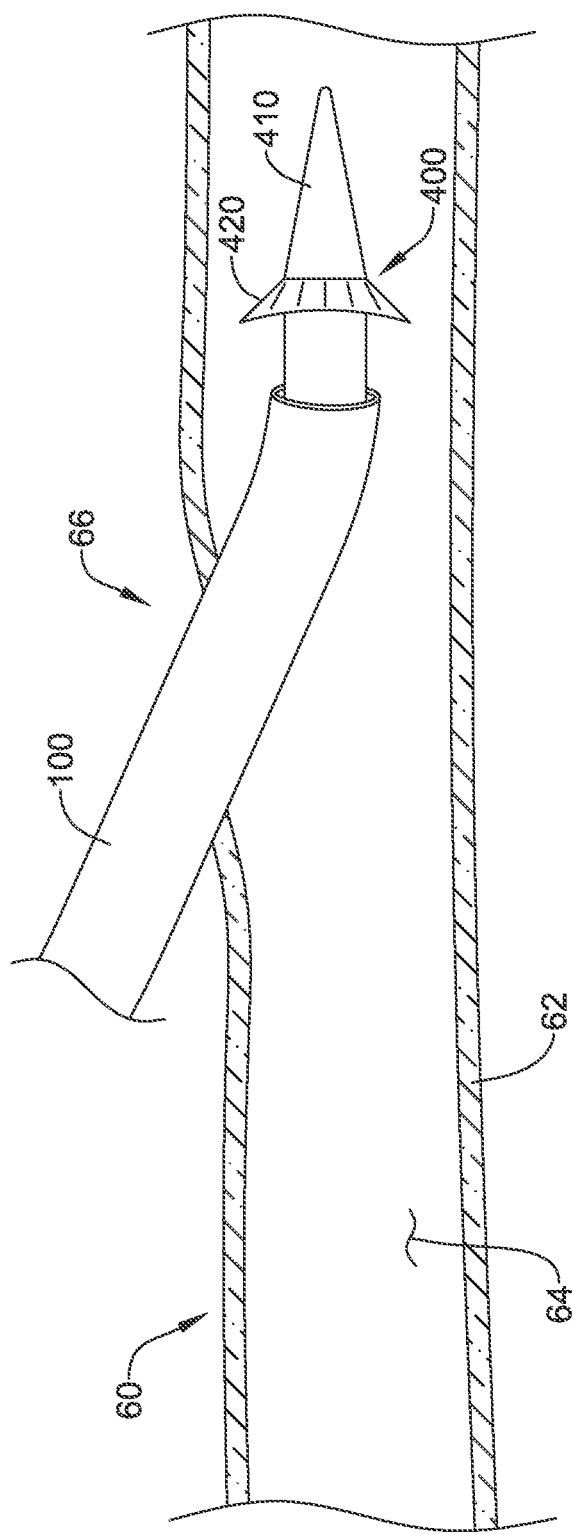
FIG. 5 illustrates the example introducer sheath of FIG. 4 extending through an opening in a blood vessel wall.

As may be seen in FIG. 5 for example, the introducer sheath 100 may extend through the opening 66 in the wall 62 of the blood vessel 60 or other tubular structure. The introducer sheath 100 may be used as a conduit to access the lumen 64 of the blood vessel 60 or other tubular structure with a percutaneous medical device 200 (not shown) to perform an intravascular procedure at a target site. Upon completion of the procedure, the percutaneous medical device 200 may be removed and closure of the opening 66 in the wall 62 of the blood vessel 60 or other tubular structure may be effected. In some embodiments, closure of the opening 66 in the wall 62 of the blood vessel 60 may be preceded by placing the dilator 400 through the lumen (e.g., 120, FIG. 1) of the introducer sheath 100 and the enlargeable portion 420 in the everting configuration, as seen in FIG. 3 for example. In some embodiments, the enlargeable portion 420 may be configured to collapse radially inward toward and/or against an outer surface of the dilator 400 to facilitate passing the dilator 400 and/or the enlargeable portion 420 through the lumen 120 of the introducer sheath 100. In some embodiments, placing the enlargeable portion 420 into the everting configuration may include expanding and/or inflating the enlargeable portion 420 (if capable thereof) such that the enlargeable portion 420 extends radially outward from the outer wall 110 of the introducer sheath 100 after the enlargeable portion 420 of the dilator 400 has been passed through the introducer sheath 100. In the everting configuration, the enlargeable portion 420 may contact, engage, and/or otherwise pull tissue of the blood vessel 60 or other tubular structure outward (e.g., evert) at the opening 66 in the wall 62 of the blood vessel 60 or other tubular structure as the dilator 400 and/or the introducer sheath 100 is withdrawn from the lumen 64 of the blood vessel 60 or other tubular structure through the opening 66 in the wall 62 of the blood vessel 60 or other tubular structure.

Figure 6:
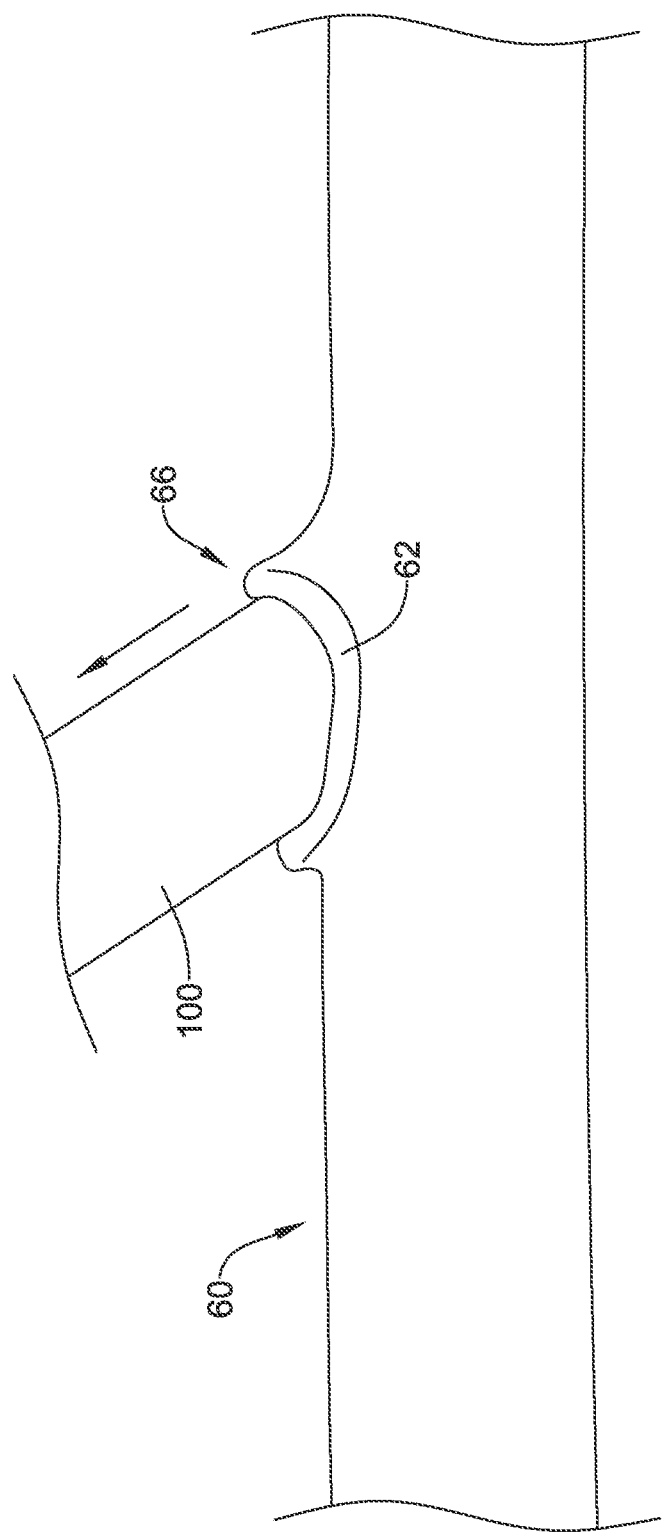
FIG. 6 illustrates eversion of tissue of a blood vessel as an example introducer sheath in accordance with the disclosure is partially withdrawn through an opening in the blood vessel wall.

FIG. 6 illustrates tissue of the wall 62 of the blood vessel 60 or other tubular structure being everted as the introducer sheath 100 and/or the dilator 400 (not shown) is partially withdrawn from the lumen of the blood vessel 60 or other tubular structure. The enlargeable portion 130/420 (not shown) engages the edge(s) of the tissue and pulls the edge(s) outward away from the lumen of the blood vessel 60 or other tubular structure due to its larger radial extent and/or surface feature(s) configured to attach, adhere, and/or "stick" tissue thereto when withdrawn and/or retracted in a proximal direction through the opening 66 in the wall 62 of the blood vessel 60 or other tubular structure.

Figure 7:
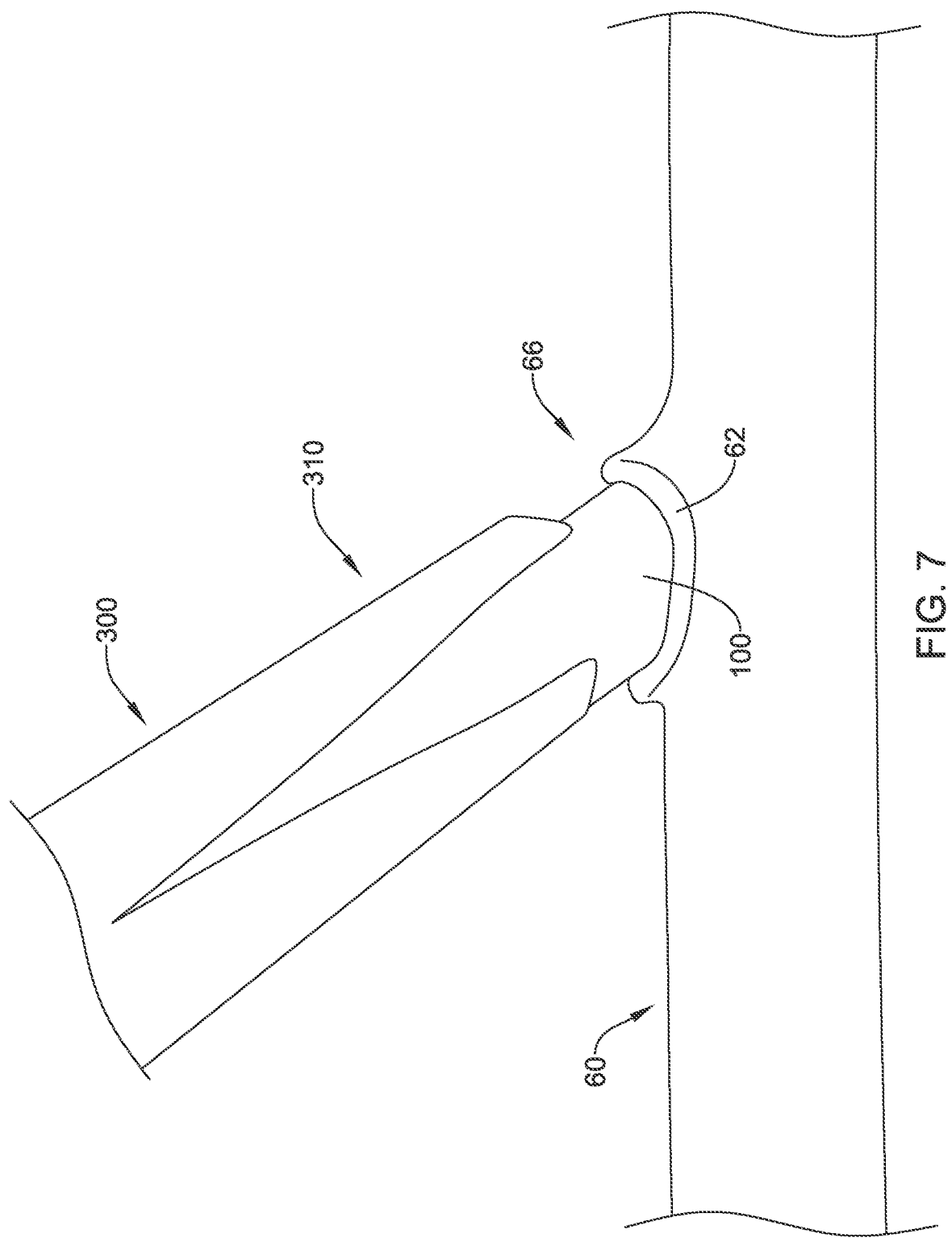
FIG. 7 illustrates an example shaping sheath disposed over an example introducer sheath.
Figure 8:
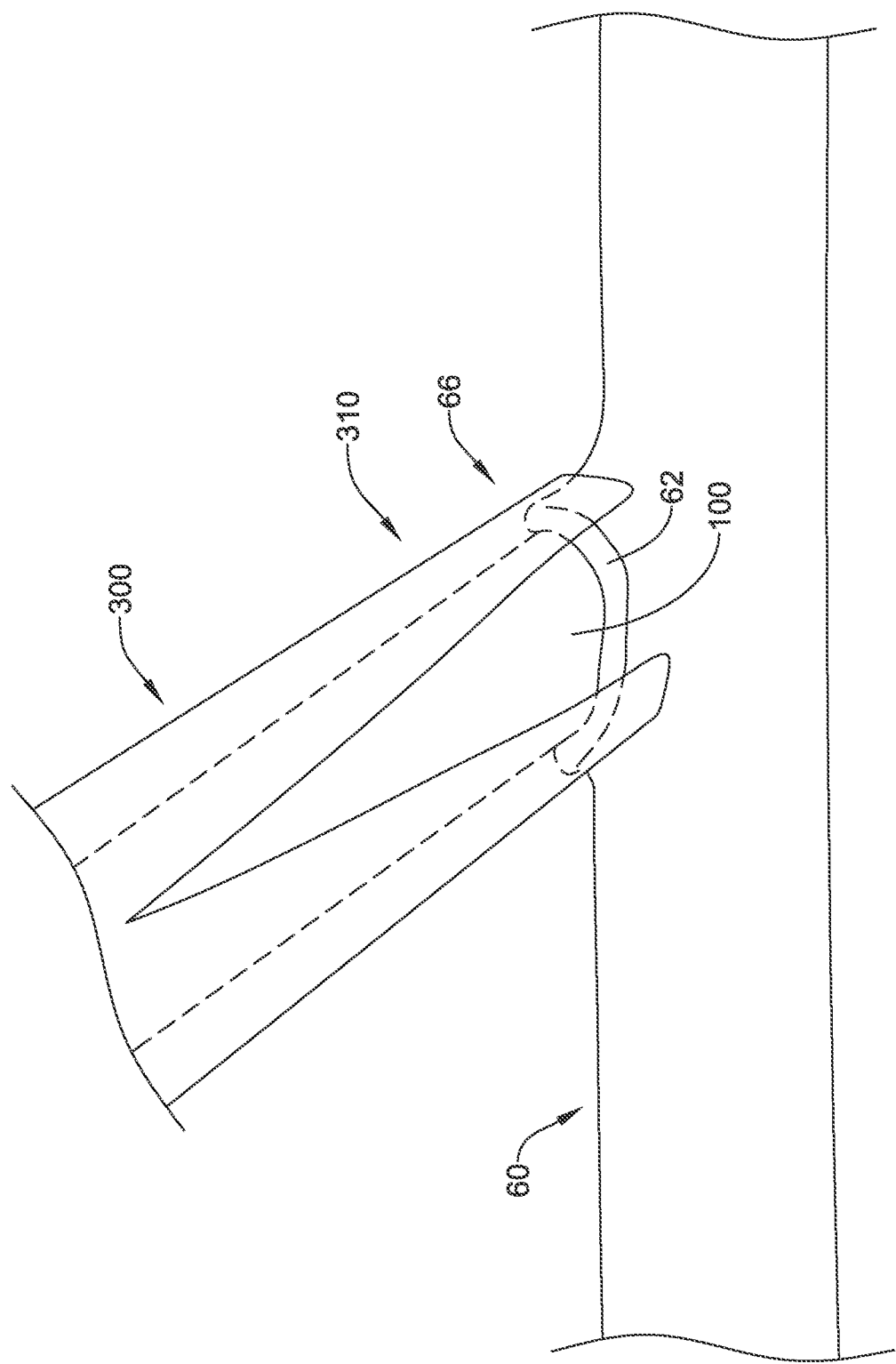
FIG. 8 illustrates an example shaping sheath engaged with a blood vessel.
Figure 9:
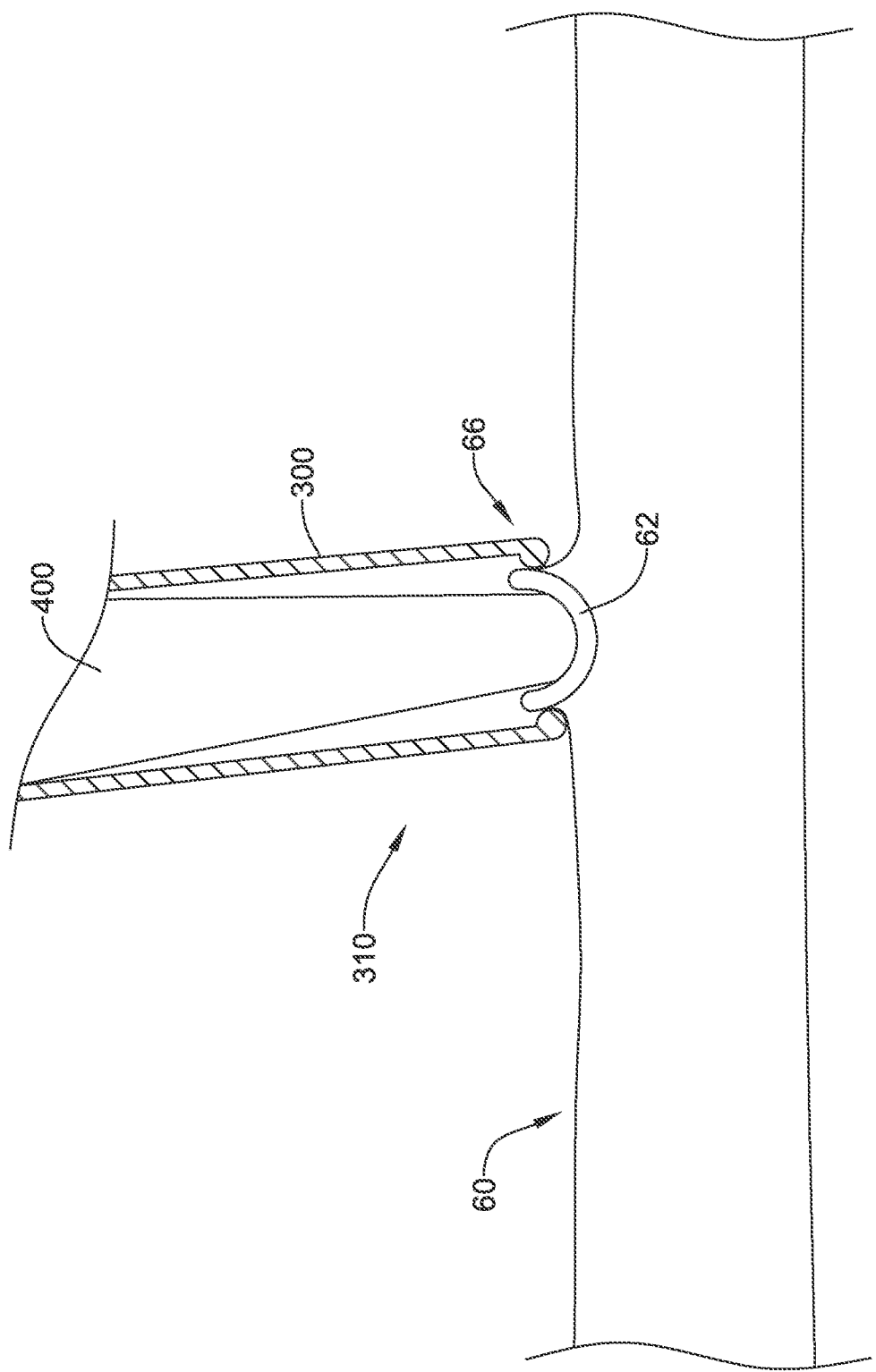
FIG. 9 illustrates an example shaping sheath engaged with a blood vessel as an example introducer sheath is being withdrawn from the blood vessel.

FIG. 7 illustrates a shaping sheath 300 disposed over an introducer sheath 100 extending through the opening 66 in the wall 62 of the blood vessel 60 or other tubular structure at a position spaced apart from and/or proximal of an outer surface of the wall 62 of the blood vessel 60 or other tubular structure. Constructional details of the shaping sheath 300 will be discussed in more detail below. The shaping sheath 300 may be advanced over the introducer sheath 100 before or after the introducer sheath 100 and/or the dilator 400 is partially withdrawn through the opening 66 in the wall 62 of the blood vessel 60 or other tubular structure. After partially withdrawing the introducer sheath 100 and/or the dilator 400 (not shown) from the lumen 64 of the blood vessel 60 or other tubular structure, the shaping sheath 300 may be advanced over the introducer sheath 100 to the opening 66 in the wall 62 of the blood vessel 60 or other tubular structure, where the split distal portion 310 of the shaping sheath 300 engages the outer surface of the wall 62 of the blood vessel 60 or other tubular structure, as seen in FIG. 8 for example. The split distal portion 310 may be configured to engage and/or grip the everted tissue of the opening 66 in the wall 62 of the blood vessel 60 or other tubular structure. In some embodiments, withdrawal of the introducer sheath 100, the percutaneous medical device 200 (not shown), and/or the dilator 400 (not shown) from within the shaping sheath 300 permits the split distal portion 310 of the shaping sheath 300 to translate the everted tissue to bring an inner surface of the wall 62 of the blood vessel 60 or other tubular structure into contact with itself along a transverse seam relative to a longitudinal axis of the lumen 64 of the blood vessel 60 or other tubular structure. It may be desirable for the inner surface of the wall 62 of the blood vessel 60 or other tubular structure to contact itself during closure of the opening 66 in order to preserve the endothelium and/or to facilitate healing. In some embodiments, progressively withdrawing the dilator 400 from within the shaping sheath 300, as shown in FIG. 9 for example, may permit the split distal end 310 of the shaping sheath 300 to pull the everted tissue into a transverse oval shape. A transverse seam or closure line may be beneficial for limiting or preventing a reduction in a cross-sectional extent of the lumen 64 of the blood vessel 60 or other tubular structure. It has been found that in some cases, a longitudinally-oriented seam or closure line may result in a reduction in the cross-sectional extent of the lumen of the blood vessel 60 at the site of the opening 66 and/or the closure thereof.

Figure 10:
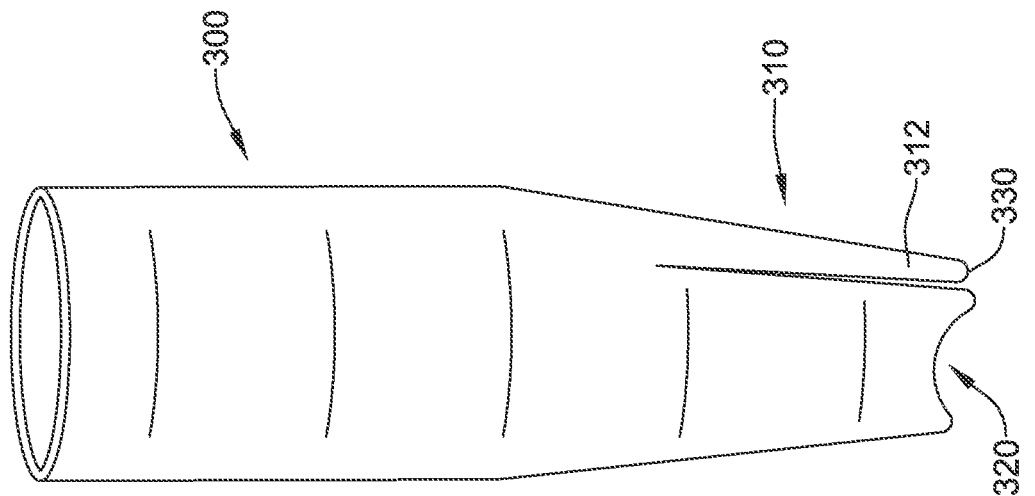
FIG. 10 illustrates an example shaping sheath.

FIG. 10 illustrates an example of the shaping sheath 300 having a split distal portion 310 at and/or adjacent to a concave distal end 320 of the shaping sheath 300. The split distal portion 310 may be configured to engage and/or grip the everted tissue of the opening in the wall of the blood vessel or other tubular structure, as discussed above. In some embodiments, the shaping sheath 300 may include a concave distal end 320 configured to conform to and/or to engage the outer surface of the wall of the blood vessel or other tubular structure. As illustrated, the split distal portion 310 may comprise two opposing sides 312 or fingers each biased radially inward and/or sufficiently flexible to permit bending or flexing radially outward when disposed over the introducer sheath 100 and/or the dilator 400. However, in some embodiments, the split distal portion 310 may comprise more than two sides 312 or fingers (e.g., three, four, five, six, eight, ten, etc.) each biased radially inward and/or sufficiently flexible to permit bending or flexing radially outward when disposed over the introducer sheath 100 and/or the dilator 400, as seen in FIGS. 7 and 8 for example. In some embodiments, each side 312 or finger of the split distal portion 310 may be self-biased radially inward.

Figure 11:
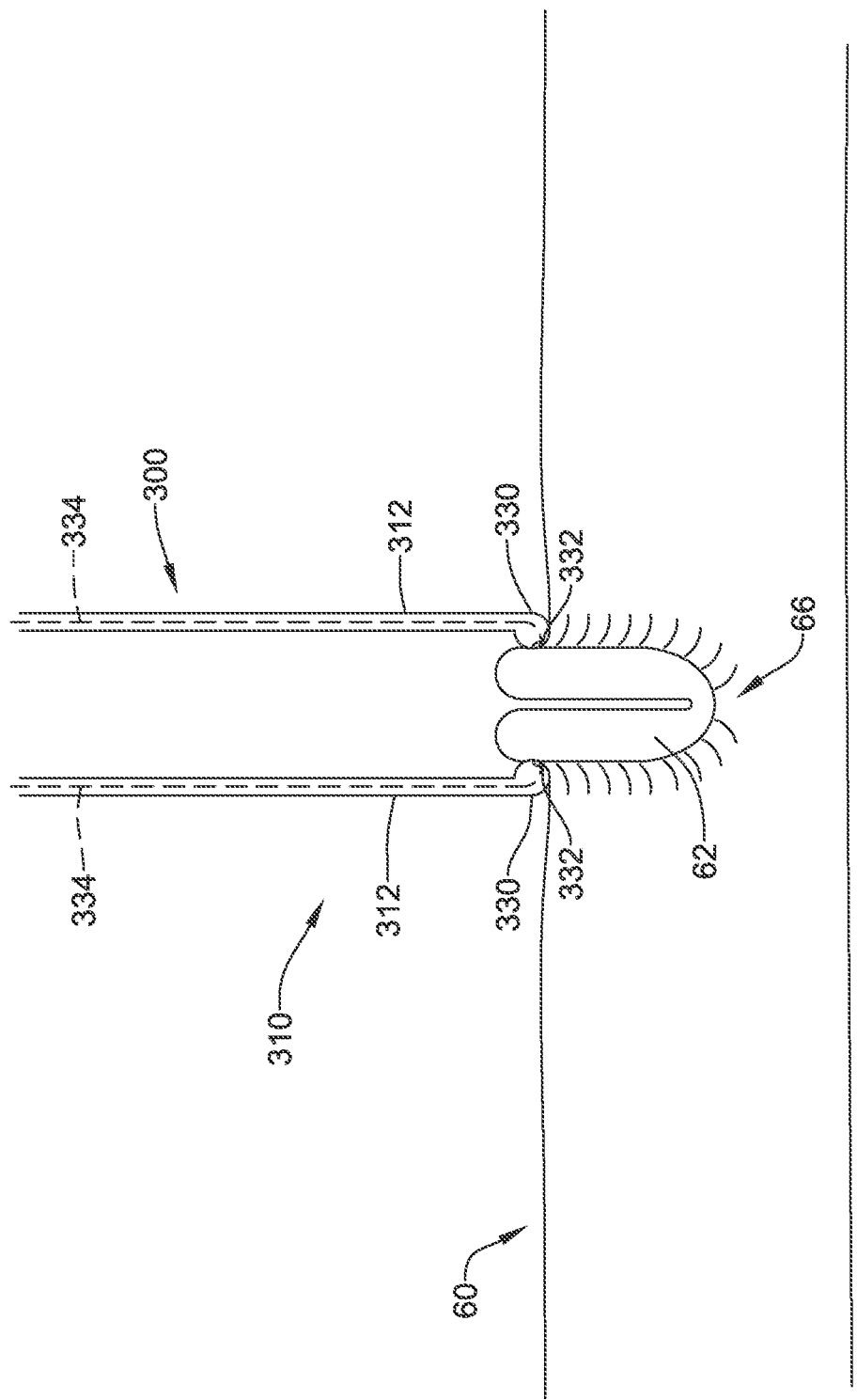
FIG. 11 illustrates a portion of an example shaping sheath engaged with a blood vessel.
Figure 12:
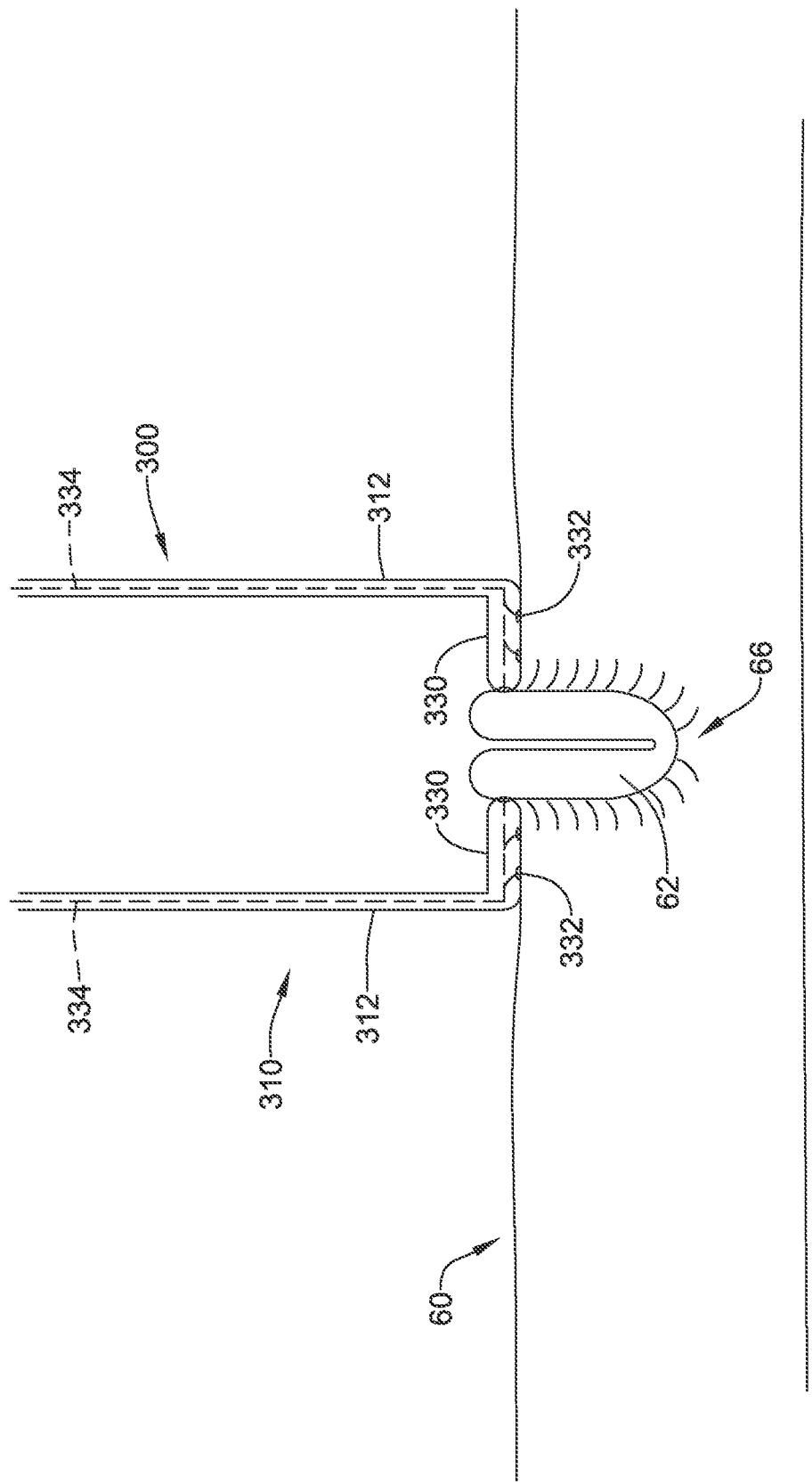
FIG. 12 illustrates a portion of an example shaping sheath engaged with a blood vessel.

In some embodiments, each side 312 or finger of the split distal portion 310 may include a lip 330 extending radially inward from its respective side or finger. A width of the lip 330 may vary, as seen in FIGS. 11 and 12. In some embodiments, the width of the lip 330 may accommodate later steps in the closure process, for example, a stapler or other securing device being advanced within the shaping sheath 300, as will be discussed in more detail below. In some embodiments, the lip 330 may include one or more suction port(s) 332, thereby forming a suction rim at the concave distal end 320 (e.g., FIG. 10) of the shaping sheath 300. In some embodiments, the one or more suction port(s) 332 may face distally. In some embodiments, the one or more suction port(s) 332 may face radially inward. In some embodiments, the one or more suction port(s) 332 may face distally and radially inward. Each side or finger of the split distal portion 310 may have one or more suction lumens 334 extending from the one or more suction port(s) 332 to a proximal end of the shaping sheath 300. In some embodiments, each of the one or more suction lumens 334 may converge into a single main suction lumen within a wall of the shaping sheath 300 that extends to a proximal suction port for connection to a source of suction. In some embodiments, some or all of the one or more suction lumens 334 may extend from the one or more suction port(s) 332 of the lip 330 to the proximal suction port, or a plurality of proximal suction ports. The one or more suction port(s) 332 may permit the split distal portion 310 and/or the suction rim of the shaping sheath 300 to engage and/or to be secured to and/or grip the everted tissue.

In addition or alternatively, in some embodiments, each side or finger of the split distal portion 310 may include one or more magnets attached thereto and/or embedded therein. The one or more magnets may be configured to attract each side or finger of the split distal portion 310 toward each other to engage and/or hold and/or grip the everted tissue.

In addition or alternatively, in some embodiments, the shaping sheath 300 may include an outwardly-flared split distal portion and/or a distal taper toward a greater outer extent or diameter. In some embodiments, a closing sheath (not shown) may be slidably advanced over the shaping sheath 300 to act as a collet mechanism, thereby forcing the distal portion of the shaping sheath 300 radially inward against the everted tissue to thereby engage and/or grip the everted tissue.

In addition or alternatively, in some embodiments, the shaping sheath 300 may include an un-split and/or annular distal portion having a shape memory element attached thereto and/or disposed or embedded therein. The shape memory element may be configured to close and/or transform the distal end of the shaping sheath 300 to a flattened shape as the dilator 400 is removed and/or withdrawn therefrom.

Figure 13:
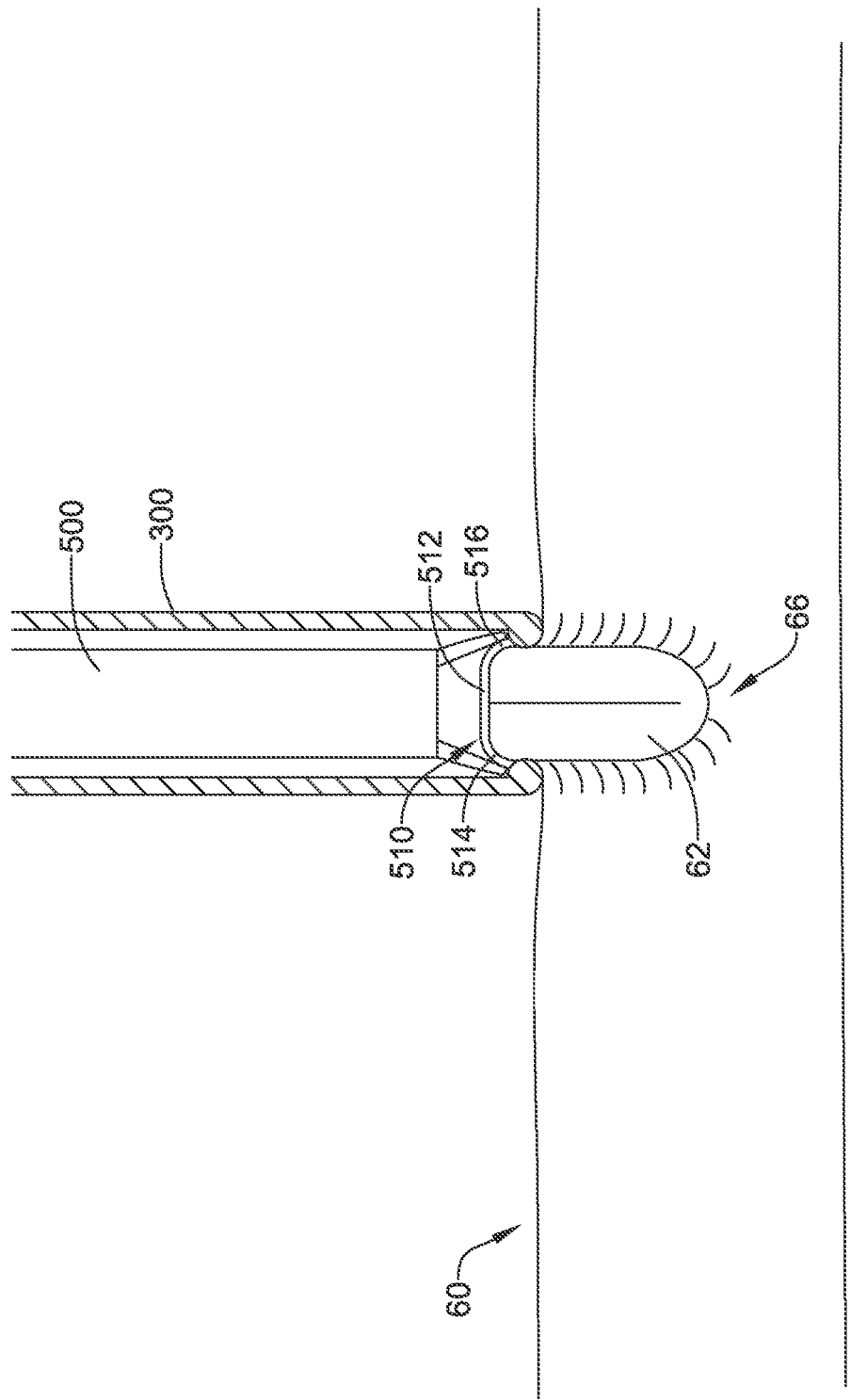
FIG. 13 illustrates an example stapler disposed within the shaping sheath.

FIG. 13 schematically illustrates an example stapler 500 which may be used in conjunction with the system and/or device(s) described above. While the following discussion is made with respect to the stapler 500 in the interest of brevity, other fastening means (e.g., sutures, clips, pins, etc.) may also be utilized within the scope of this disclosure. The stapler 500 may be configured to be slidably disposed within the shaping sheath 300 for fastening the everted tissue. In some embodiments, the stapler 500 may include a distal stapler head configured to deform staples into a secured configuration. In some embodiments, the stapler 500 may be advanced within the shaping sheath 300 to the everted tissue at the opening 66 in the wall 62 of the blood vessel 60 or other tubular structure. In some embodiments, the stapler 500 may comprise multiple parallel staplers each configured to deploy one or more staples 510 into the everted tissue. In some embodiments, the multiple parallel staplers may include multiple stapler heads within a single stapler, wherein each stapler head is configured to deploy one staple 510 at a time. In some embodiments, the stapler 500 may include multiple staples 510 arranged in parallel within a single stapler and/or stapler head. In some embodiments, the stapler 500 may be configured to deploy multiple staples 510 in succession, in series, and/or simultaneously into the everted tissue. The staples 510 may each include a body 512 having a first leg 514 extending in a first direction from a first end of the body and a second leg 516 extending in the first direction from a second end of the body. The staples 510 may be configured to be deformed from a delivery configuration to a secured configuration, wherein in the secured configuration the first leg 514 and/or the second leg 516 are bent in a second direction away from the first direction and wherein a free end of the first leg 514 extends generally toward a free end of the second leg 516.

Figure 14:
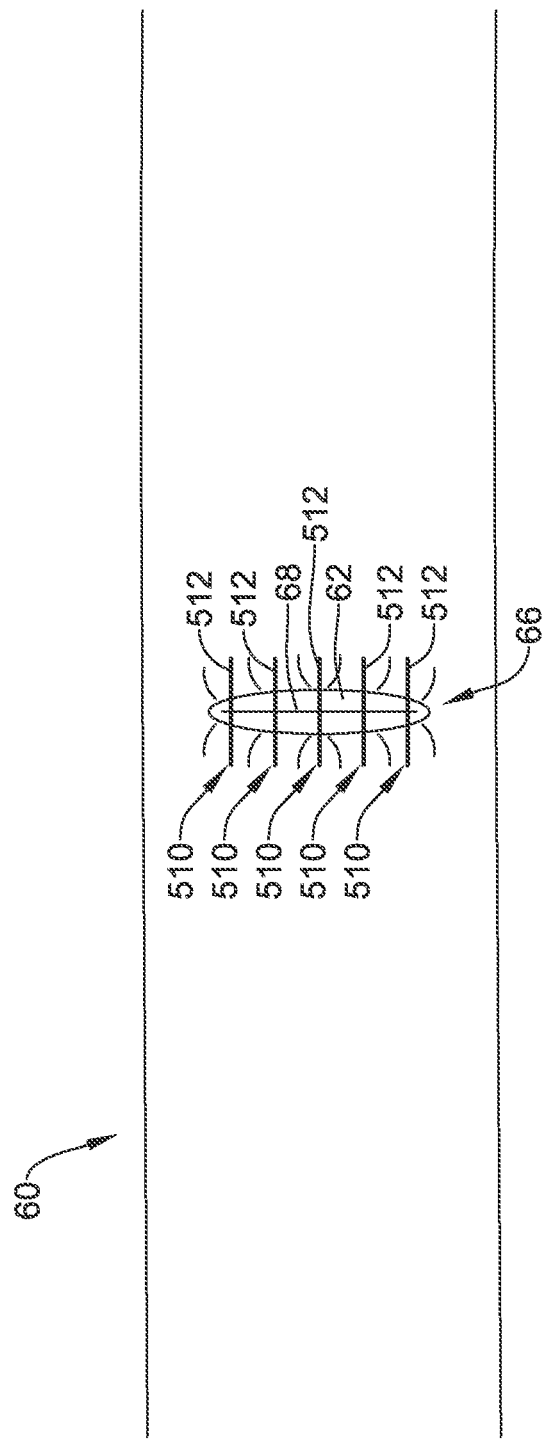
FIG. 14 illustrates an example closure of an opening in a blood vessel.

In some embodiments, the body 512 of each of the staples 510 may be oriented parallel to a longitudinal axis of the lumen of the blood vessel 60 or other tubular structure, as seen relative to a transverse seam 68 of the everted tissue at the opening 66 in the wall 62 of the blood vessel 60 or other tubular structure in FIG. 14 for example. In some embodiments, the body 512 of each of the staples 510 may be transverse to the longitudinal axis of the lumen of the blood vessel 60 or other tubular structure and the first direction may be parallel to the longitudinal axis of the lumen of the blood vessel 60 or other tubular structure, as seen in FIGS. 15-20 for example (described further below). It is noted that when closing large bore punctures, a single fastener (e.g., staple, suture, spring clips, etc.) may be insufficient to properly and/or completely close the opening 66. In some instances, multiple fasteners (e.g., staples, sutures, spring clips, etc.) may be required to properly and/or completely close the opening 66 in the wall 62 of the blood vessel 60 or other tubular structure. While FIG. 14 illustrates five fasteners (e.g., staples 510, etc.), other quantities of fasteners may be used—such as, but not limited to, two, three, four, six, eight, ten, etc. — as well as combinations of fasteners, such as staples and sutures, for example. In some embodiments, the fasteners may be formed from a biodegradable and/or biocompatible material.

In some embodiments, a bioadhesive may be applied to the everted tissue upon closure of the opening 66 in the wall 62 of the blood vessel 60 or other tubular structure to further seal the opening 66 along the transverse seam 68. In some embodiments, the bioadhesive may be applied to the everted tissue after the fasteners (e.g., staples, sutures, spring clips, etc.) are applied to and/or installed at the opening 66 in the wall 62 of the blood vessel 60 or other tubular structure to further seal the opening 66 along the transverse seam 68. In some embodiments, a bioadhesive applicator may be inserted through the shaping sheath 300 after the stapler 500 is removed, and a separate compressor and/or spreader element may be used thereafter to spread and/or apply compressive force to the bioadhesive and the everted tissue. In some embodiments, the bioadhesive may be used in place of the fasteners (e.g., staples, sutures, spring clips, etc.) to seal the opening 66 along the transverse seam 68.

In some embodiments, after closing the opening 66 in the wall 62 of the blood vessel 60 or other tubular structure, a removal device may be inserted into the shaping sheath 300 to spread apart the split distal portion 310, thereby releasing the everted tissue and permitting withdrawal of the shaping sheath 300. In some embodiments, the removal device may include and/or be selected from a non-tapered catheter or shaft, the dilator 400, the stapler 500, or other suitable device. Other suitable devices are contemplated and the above list is not intended to be limiting.

Figure 15:
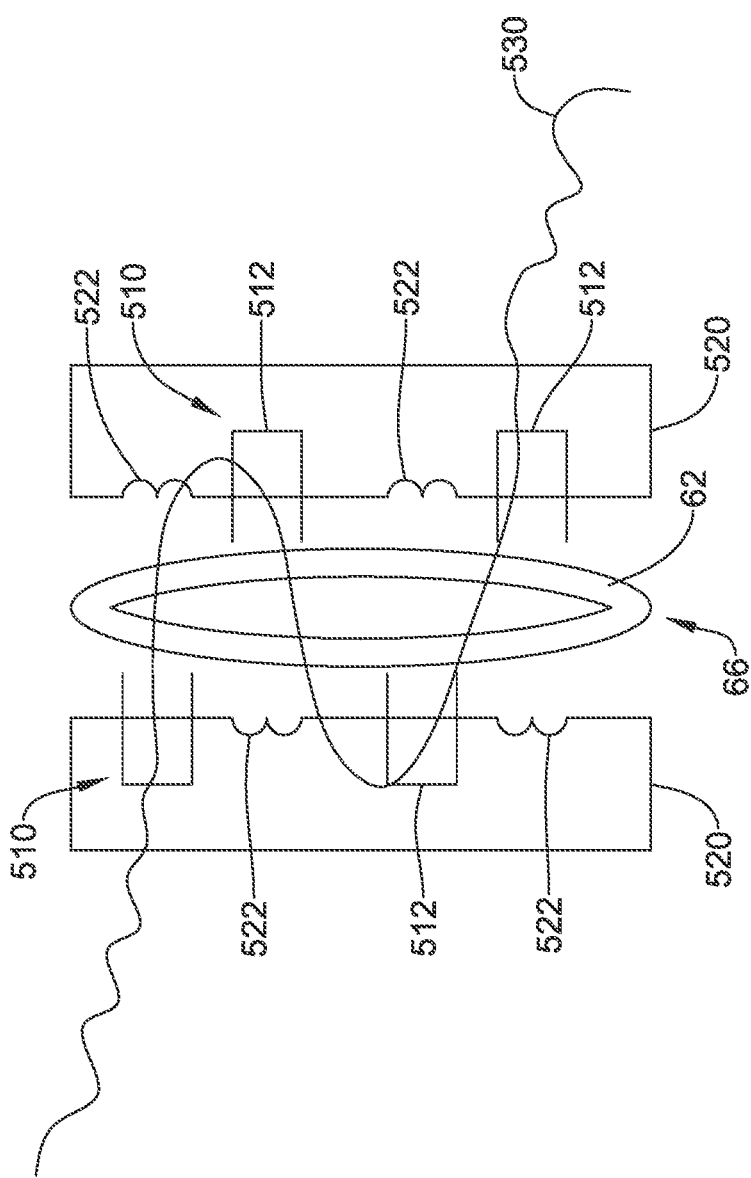
FIGS. 15-17 illustrate an example configuration for closing an opening in a blood vessel.
Figure 16:
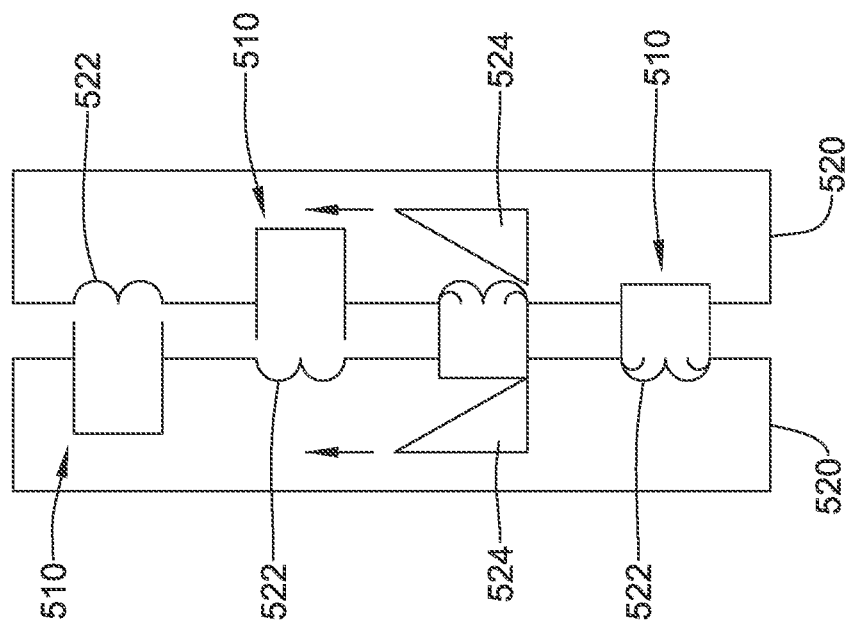
Figure 17:
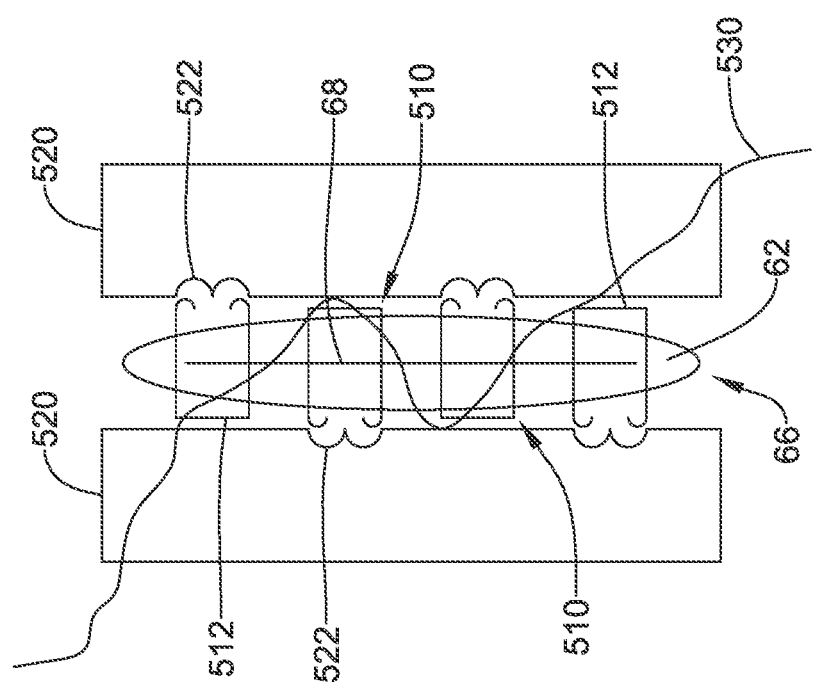

FIGS. 15-17 illustrate aspects of an example configuration for closing the opening 66 in the wall 62 of the blood vessel or other tubular structure. In general, everted tissue and/or the transverse seam 68 may be formed as described above. In some embodiments, staples 510 may be positioned upstream and downstream of the transverse seam 68 of the everted tissue at the opening 66 in the wall 62 of the blood vessel or other tubular structure in the delivery configuration. The body 512 of the staples 510 may be oriented transverse to the longitudinal axis of the lumen 64 of the blood vessel or other tubular structure, and the first and second legs of the staples 510 may be oriented with the first direction parallel to the longitudinal axis of the lumen of the blood vessel or other tubular structure. In some embodiments, a suture 530 may be threaded through, anchored by, and/or connected to the staples 510, as discussed further below. The body 512 of each staple 510 may be held by, or in contact with, one of two opposing jaws 520 of a stapler 500. At a position opposite the body 512 of each staple 510 in the first direction, forming features 522 may be disposed in the other opposing jaw 520. The forming features 522 may be configured to deform the staple(s) 510 from the delivery configuration to the secured configuration. The forming features 522 may be configured to bend the first and second legs in the second direction away from the first direction and/or such that the free end of the first leg and the free end of the second leg extend toward each other. In some embodiments, the second direction may be about 90 degrees relative to the first direction. Other configurations are also contemplated.

In some embodiments, the opposing jaws 520 may be translated toward each other, by actuating the stapler 500 for example, from an initial position toward and/or to an actuated position. In some embodiments, one or each opposing jaw 520 may include an inflatable balloon configured to advance a pusher plate toward the staple(s) 510, thereby advancing the staple(s) 510 toward the forming features 522 on the other opposing jaw 520 to deform the staple(s) 510 from the delivery configuration to the secured configuration.

In some embodiments, the opposing jaws 520 may include a slidable actuation mechanism to deform the staple(s) 510 from the delivery configuration to the secured configuration, as seen in FIG. 16 for example. In some embodiments, each opposing jaw 520 may include a wedge-shaped runner 524 configured to slide along its respective opposing jaw 520 from a first end to a second end. As the wedge-shaped runner 524 is slid along it respective opposing jaw 520, each staple 510 may be gradually pushed away from the opposing jaw 520 it is held by or in contact with toward the other opposing jaw 520 and/or the forming features 522 to deform the staple(s) 510 from the delivery configuration to the secured configuration. Engagement of the first and second legs with the forming features 522 by the wedge-shaped runner 524 may cause the first and second legs to bend in the second direction away from the first direction and/or such that the free end of the first leg and the free end of the second leg extend toward each other, as seen in FIG. 17 for example.

In some embodiments, a suture 530 may be threaded through, anchored by, and/or connected to the staples 510. In some embodiments, the suture 530 may pass between the everted tissue and the body 512 of each staple 510, and over or under at least one of the first leg and the second leg. Placing the suture 530 in tension (such as by pulling on opposing ends of the suture 530, for example) the everted tissue on opposing sides of the transverse seam 68 may be pulled together. Similar to FIG. 14 above, while four fasteners (e.g., staples 510, etc.) are illustrated in FIGS. 15-17, other quantities of fasteners may be used—such as, but not limited to, two, three, four, six, eight, ten, etc.

Figure 18:
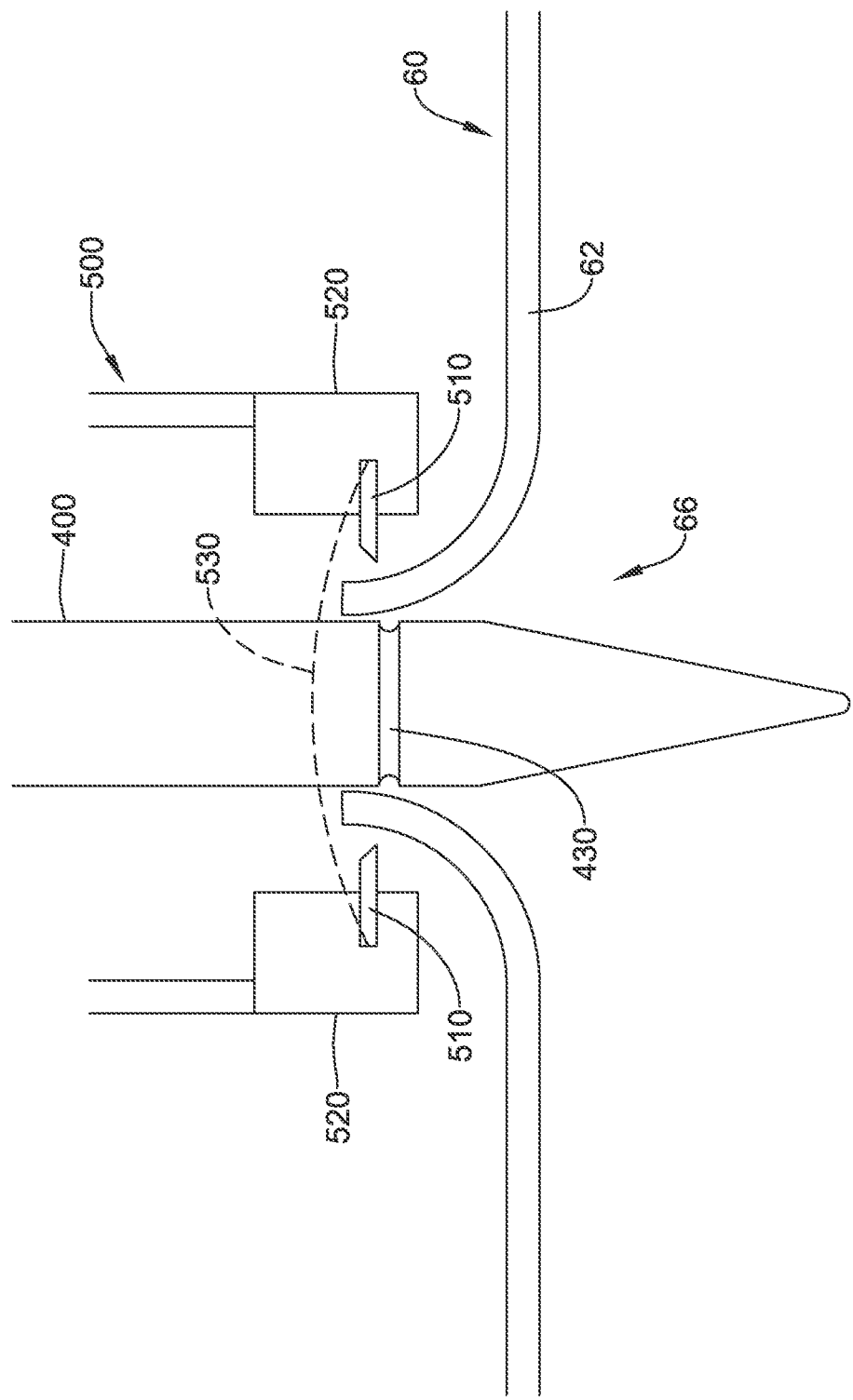
Figure 19:
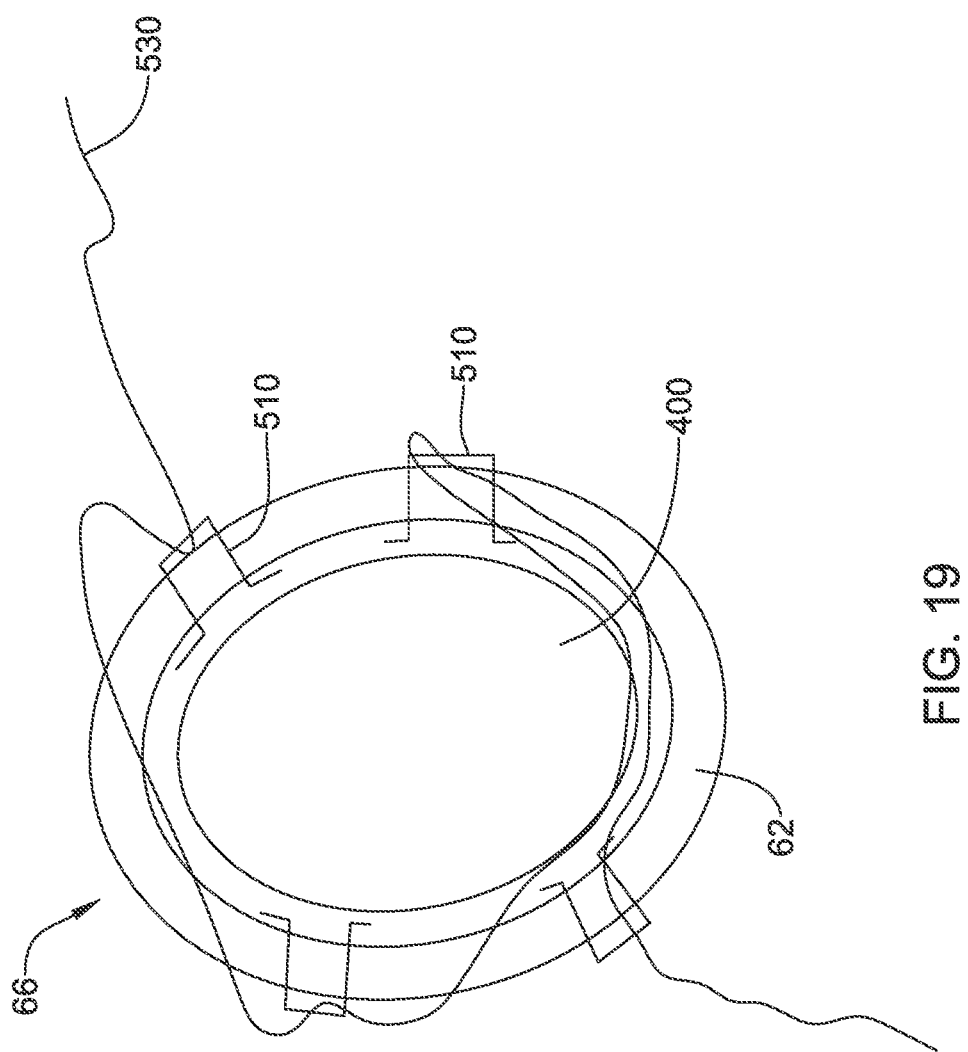

FIGS. 18-20 illustrate aspects of an example configuration for closing the opening 66 in the wall 62 of the blood vessel 60 or other tubular structure. In general, everted tissue may be formed as described above. In some embodiments, the configuration shown in FIGS. 18-20 may be used in conjunction with the dilator 400 in place within the opening 66 in the wall 62 of the blood vessel 60 or other tubular structure, as seen in FIG. 18 for example. In some embodiments, staples 510 may be positioned upstream and downstream of the opening 66 in the wall 62 of the blood vessel 60 or other tubular structure in the delivery configuration. The body of the staples 510 may be oriented generally transverse to the longitudinal axis of the lumen of the blood vessel 60 or other tubular structure, and the first and second legs of the staples 510 may be oriented with the first direction generally parallel to the longitudinal axis of the lumen of the blood vessel 60 or other tubular structure. The body of each staple 510 may be held by, or in contact with, one of two opposing jaws 520 of the stapler 500. At a position opposite the body of each staple 510 in the first direction, the dilator 400 may include a groove 430 or other forming feature disposed around a circumference of the dilator 400. The groove 430 or other forming feature may be configured to deform the staple(s) 510 from the delivery configuration to the secured configuration. In some embodiments, the groove 430 or other forming feature may be configured to bend the first and second legs in the second direction away from the first direction and/or such that the free end of the first leg and the free end of the second leg extend toward each other, similar to the discussion above. In some embodiments, the groove 430 or other forming feature may be configured to bend the first and second legs in the second direction away from the first direction and/or such that the free end of the first leg and the free end of the second leg extend away from each other, as seen in FIG. 19 for example. In some embodiments, the second direction may be about 90 degrees relative to the first direction. Other configurations are also contemplated.

In some embodiments, a suture 530 may be threaded through, anchored by, and/or connected to the staples 510. In some embodiments, the suture 530 may pass between the everted tissue and the body of each staple 510, and over or under at least one of the first leg and the second leg. Placing the suture 530 in tension (such as by pulling on opposing ends of the suture 530, for example) the everted tissue on opposing sides of the transverse seam 68 may be pulled together. During deformation of the staple(s) 510 and/or with the dilator 400 in place within the opening 66 in the wall 62 of the blood vessel 60 or other tubular structure, the suture 530 may extend at least partially around the circumference of the dilator 400. As the opposing jaws 520 are translated toward each other from an initial position toward and/or to an actuated position, the dilator 400 may be withdrawn from the opening 66 in the wall 62 of the blood vessel 60 or other tubular structure. In some embodiments, the staple(s) 510 in the secured configuration may extend through everted tissue on only one side of the transverse seam 68, and tension placed on the suture 530 may draw the everted tissue on opposing sides of the transverse seam together, as seen in FIG. 20 for example. As such, in at least some embodiments, the staple(s) 510 may act as anchors or posts in the everted tissue about which the suture 530 extends. Similar to FIG. 14 above, while four fasteners (e.g., staples 510, etc.) are illustrated in FIGS. 18-20, other quantities of fasteners may be used—such as, but not limited to, two, three, four, six, eight, ten, etc.

The materials that can be used for the various components of the introducer sheath 100, the percutaneous medical device 200, the shaping sheath 300, the dilator 400, etc. (and/or other systems disclosed herein) and the various elements thereof disclosed herein may include those commonly associated with medical devices. For simplicity purposes, the following discussion makes reference to the introducer sheath 100, the percutaneous medical device 200, the shaping sheath 300, the dilator 400, etc. However, this is not intended to limit the devices and methods described herein, as the discussion may be applied to other elements, members, components, or devices disclosed herein, such as, but not limited to, the introducer sheath 100, the percutaneous medical device 200, the shaping sheath 300, the dilator 400, etc. and/or elements or components thereof.

In some embodiments, the introducer sheath 100, the percutaneous medical device 200, the shaping sheath 300, the dilator 400, etc., and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the introducer sheath 100, the percutaneous medical device 200, the shaping sheath 300, the dilator 400, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the introducer sheath 100, the percutaneous medical device 200, the shaping sheath 300, the dilator 400, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the introducer sheath 100, the percutaneous medical device 200, the shaping sheath 300, the dilator 400, etc. to achieve the same result.

In some embodiments, a degree of Magnetic Resonance Imaging (Mill) compatibility is imparted into the introducer sheath 100, the percutaneous medical device 200, the shaping sheath 300, the dilator 400, etc. For example, the introducer sheath 100, the percutaneous medical device 200, the shaping sheath 300, the dilator 400, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The introducer sheath 100, the percutaneous medical device 200, the shaping sheath 300, the dilator 400, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the introducer sheath 100, the percutaneous medical device 200, the shaping sheath 300, the dilator 400, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:
1. A vascular closure system for sealing an opening in a blood vessel, comprising:
an introducer sheath configured to extend through the opening in the blood vessel the introducer sheath having a lumen extending through the introducer sheath;

wherein partial withdrawal of the introducer sheath from the opening is configured to evert tissue of the blood vessel at the opening in the blood vessel;

a shaping sheath slidably disposed over the introducer sheath, the shaping sheath having a split distal portion configured to engage the everted tissue; and a dilator configured to be slidably received within the lumen of the introducer sheath, wherein the dilator includes an enlargeable portion proximate a tapered distal end of the dilator, and wherein the introducer sheath includes an enlargeable portion proximate a distal end of the introducer sheath.

2. The vascular closure system of claim 1, wherein the shaping sheath includes a concave distal end configured to engage an outer surface of the blood vessel.

3. The vascular closure system of claim 1, wherein each side of the split distal portion of the shaping sheath is biased radially inward.

4. The vascular closure system of claim 1, wherein the split distal portion is configured to engage the everted tissue to form a seam oriented transverse to a longitudinal axis of the blood vessel.

5. The vascular closure system of claim 1, wherein the shaping sheath includes a suction rim at a distal end of the shaping sheath configured to secure the split distal portion to the everted tissue.

6. The vascular closure system of claim 1, further comprising a stapler configured to be slidably disposed within the shaping sheath for fastening the everted tissue.

7. The vascular closure system of claim 6, wherein the stapler comprises multiple parallel staplers each configured to deploy one or more staples into the everted tissue.

8. The vascular closure system of claim 6, wherein the stapler is configured to deploy multiple staples in series into the everted tissue.

9. The vascular closure system of claim 1, further comprising a percutaneous medical device configured to be slidably disposed within the lumen to perform an intravascular procedure, wherein withdrawal of the introducer sheath and the percutaneous medical device from within the shaping sheath permits the split distal portion to translate the everted tissue to bring an inner surface of the blood vessel into contact with itself.

10. The vascular closure system of claim 1, wherein the enlargeable portion of the introducer sheath extends radially outward from the introducer sheath at a maximum outer extent of the enlargeable portion.

11. The vascular closure system of claim 1, wherein the enlargeable portion of the dilator is configured to extend radially outward from the introducer sheath after the enlargeable portion of the dilator has been passed through the introducer sheath.

* * * * *